(12) United States Patent
Ozaki et al.

(10) Patent No.: US 6,201,009 B1
(45) Date of Patent: Mar. 13, 2001

(54) ABSORPTION-ENHANCING COMPOSITION FOR PANTOTHENIC ACID DERIVATIVE

(75) Inventors: Masahiro Ozaki; Miwako Hagiuda; Daiichi Watanabe, all of Tokyo (JP)

(73) Assignee: Fujirebio Inc., Tokyo (JP)

( * ) Notice: Subject to any disclaimer, the term of this patent is extended or adjusted under 35 U.S.C. 154(b) by 0 days.

(21) Appl. No.: 09/430,250

(22) Filed: Oct. 29, 1999

(30) Foreign Application Priority Data

Oct. 30, 1998 (JP) .................................................. 10-309639

(51) Int. Cl.$^7$ ........................ A61K 31/335; C07D 319/06
(52) U.S. Cl. ............................................. 514/452; 549/372
(58) Field of Search ............................... 514/452; 549/372

(56) References Cited

U.S. PATENT DOCUMENTS 5,120,738   6/1992   Ikawa et al. .

FOREIGN PATENT DOCUMENTS

WO 97/22358   6/1997   (WO) .

*Primary Examiner*—Deborah C. Lambkin
(74) *Attorney, Agent, or Firm*—Arent Fox Kintner Plotkin & Kahn, PLLC

(57) ABSTRACT

A composition showing an improved bioavailability rate of pantothenic acid derivatives represented by the following general formula and improved storage stability and being applicable as drugs over an enlarged range:

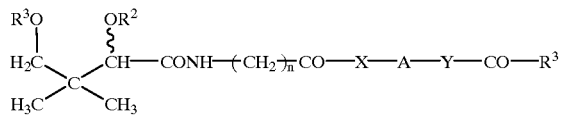

(I)

wherein $R^1$ and $R^2$ are the same or different and each represents a hydrogen atom or a hydroxyl-protective group;

$R^3$ represents a saturated or unsaturated, linear, branched or cyclic $C_{5-25}$ monovalent aliphatic hydrocarbon group optionally substituted by an aromatic group, or an amino group represented by the formula —$N(R^4)R^5$ (wherein $R^4$ represents a saturated or unsaturated, linear, branched or cyclic $C_{5-25}$ monovalent aliphatic hydrocarbon group; and $R^5$ represents a hydrogen atom or a saturated or unsaturated, linear, branched or cyclic monovalent aliphatic hydrocarbon group optionally substituted by an aromatic group);

A represents a saturated or unsaturated, linear, branched or cyclic $C_{2-16}$ divalent aliphatic hydrocarbon group, divalent aromatic hydrocarbon group or divalent heteroaryl group optionally substituted by an aromatic group;

one of X and Y represents an amino group represented by the formula —$N(R^6)$— while the other represents —O—, —S— or an amino group represented by the formula —$N(R^7)$— (wherein $R^6$ and $R^7$ represent each a hydrogen atom or a lower alkyl group); and n is an integer of from 1 to 4. The pantothenic acid derivative represented by the above general formula (I) is dissolved in a neutral or alcoholic ester and a nonionic surfactant is added thereto to give the absorption-enhancing composition.

8 Claims, No Drawings

ABSORPTION-ENHANCING COMPOSITION FOR PANTOTHENIC ACID DERIVATIVE

FIELD OF THE INVENTION

This invention relates to an absorption-enhancing composition for a pantothenic acid derivative, which comprises a pantothenic acid derivative represented by the following general formula (I), a neutral or alcoholic ester, and a nonionic surfactant:

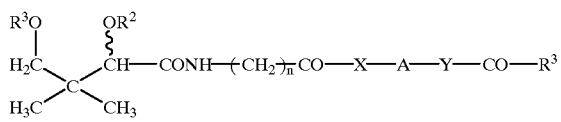

(I)

wherein
$R^1$ and $R^2$ are the same or different and each independently represents a hydrogen atom or a hydroxyl-protective group or $R^1$ and $R^2$ together represent a hydroxyl-protective group;

$R^3$ represents a saturated or unsaturated, linear, branched or cyclic $C_{5-25}$ monovalent aliphatic hydrocarbon group optionally substituted by an aromatic group, or an amino group represented by the formula —$N(R^4)R^5$ (wherein $R^4$ represents a saturated or unsaturated, linear, branched or cyclic $C_{3-25}$ monovalent aliphatic hydrocarbon group; and $R^5$ represents a hydrogen atom or a saturated or unsaturated, linear, branched or cyclic monovalent aliphatic hydrocarbon group optionally substituted by an aromatic group);

A represents a saturated or unsaturated, linear, branched or cyclic $C_{2-16}$ divalent aliphatic hydrocarbon group, divalent aromatic hydrocarbon group or divalent heteroaryl group optionally substituted by an aromatic group;

one of X and Y represents an amino group represented by the formula —$N(R^6)$— while the other represents —O—, —S— or an amino group represented by the formula —$N(R^7)$— (wherein $R^6$ and $R^7$ represent each a hydrogen atom or a lower alkyl group); and n is an integer of from 1 to 4.

BACKGROUND ART

The pantothenic acid derivatives represented by the above general formula (I) were found out as compounds having an inhibitory effect on acyl CoA-cholesterol-acyltransferase (ACAT) (JP-A-3-218340; the term "JP-A" as used herein means an "unexamined published Japanese patent application"). It is known that ACAT is contained in a large amount in intracellular microsomes in the liver and small intestine and participates in the intestinal absorption of cholesterol and the accumulation of cholesterol ester in cells. Accordingly, it is expected that compounds capable of inhibiting ACAT are usable as drugs having a blood lipid-lowering effect as well as an antiarteriosclerotic effect.

It has been confirmed that the pantothenic acid derivatives represented by the above general formula (I) have excellent inhibitory effect on ACAT. When orally administered, however, these compounds are scarcely absorbed via the digestive tracts and thus fail to establish any satisfactory effects.

Therefore, it has been required to develop compositions whereby the absorbability of the pantothenic acid derivatives represented by the above general formula (I) in vivo can be elevated and thus the bioavailability thereof can be improved. It has been also required to prepare the thus produced compositions into preparations in which the active compounds contained therein can be stabilized and stored over a long period of time.

SUMMARY OF THE INVENTION

The present inventors have conducted extensive studies to solve the above-mentioned problems. As a result, they have successfully found out that the pantothenic acid derivatives represented by the above general formula (I) can be improved in absorbability in vivo and can be stored over a long period of time by preparing compositions containing these pantothenic acid derivatives together with a neutral or alcoholic ester and a nonionic surfactant, thus completing the present invention.

Accordingly, the present invention provides absorption-enhancing compositions for pantothenic acid derivatives represented by the above general formula (I) prepared by dissolving the pantothenic acid derivative of the general formula (I) in a neutral or alcoholic ester or a solvent mixture thereof (i.e., a carbonic acid diester, an oxy-acid ester or a mixture thereof) and adding thereto a nonionic surfactant or a mixture thereof, thus enlarging the application range of the compound as a drug.

DETAILED DESCRIPTION OF THE INVENTION

Examples of the neutral or alcoholic ester to be used in the present invention include carbonic acid diesters and oxy-acid esters. The neutral or alcoholic ester can be used in an amount of 0.05 parts by weight or above, preferably from 0.1 to 40.0 parts by weight and still preferably 0.5 to 10.0 parts by weight, per 1 part by weight of the pantothenic acid derivative represented by the general formula (I). Either one of these neutral or alcoholic esters or a mixture thereof may be used in the present invention.

The carbonic acid diesters as described above have been employed as cosmetic components or, in the field of medicines, as solvents, plasticizers or gelling agents in oral preparations, general preparations for external use and preparations to be administered to the oral cavity. They may be classified into linear diesters and cyclic diesters. Examples of the linear diesters include dimethyl carbonate, diethyl carbonate and diisopropyl carbonate, while examples of the cyclic diesters include ethylene carbonate, propylene carbonate, etc. Either one of these esters or a mixture thereof may be employed. These carbonates or cyclic diesters are commercially available or can be easily obtained.

The oxy-acid esters to be used in the present invention have been employed as plasticizers for film-coating compositions for oral preparations in the field of medicines. Examples of these esters include triethyl citrate and tributyl citrate. Either one of these esters or a mixture thereof may be employed.

The nonionic surfactants to be used in the present invention have been commonly employed as emulsifiers, dispersants, etc. in the field of medicines. They may be classified into the ether type, the ether ester type, the ester type and the nitrogen-containing type. These nonionic surfactants can be used in an amount of from 0.5 to 50 parts by weight, preferably from 1 to 25 parts by weight, per 1 part by weight of the pantothenic acid derivative represented by the above general formula (I). Either one of these nonionic surfactants or a mixture thereof may be employed.

The nonionic surfactants of the ether type as described above can be further classified into, for example, polyoxyethylene alkyl ethers, polyoxyethylene alkyl aryl ethers, etc. The nonionic surfactants of the ether ester type as described above can be further classified into, for example, polyoxyethylene sorbitan fatty acid esters, polyoxyethylene glycerin fatty acid esters, etc. The nonionic surfactants of the ester type as described above can be further classified into, for example, sorbitan fatty acid esters, propylene glycol fatty acid esters, ethylene glycol fatty acid esters, ester glycerin fatty acid esters, etc. The nonionic surfactants of the nitrogen-containing type as described above can be further classified into, for example, polyoxyethylene fatty acid amides, polyoxyethylene alkylamines, etc.

Examples of the polyoxyethylene alkyl ethers include polyoxyethylene cetyl ether, polyoxyethylene oleyl ether, polyoxyethylene stearyl ether, etc. Examples of the polyoxyethylene alkyl aryl ethers include polyoxyethylene nonylphenyl ether, etc. Examples of the polyoxyethylene sorbitan fatty acid esters include polyoxyethylene sorbitan monolaurate, polyoxyethylene sorbitan monopalmitate, polyoxyethylene sorbitan monostearate, polyoxyethylene sorbitan monooleate, etc. Examples of the polyoxyethylene glycerin fatty acid esters include polyoxyethylene glycerin monostearate, polyoxyethylene glycerin triisostearate, etc. Examples of the hardened castor oil derivatives include polyoxyethylene-hardened castor oil 40, polyoxyethylene-hardened castor oil 50, polyoxyethylene-hardened castor oil 60, etc. Examples of the sorbitan fatty acid esters include polyoxyethylene fatty acid esters, sorbitan trioleate, sorbitan monooleate, sorbitan monostearate, sorbitan monocaprylate, etc. Examples of the propylene glycol fatty acid esters include propylene glycol monocaprylate, propylene glycol dicaprylate, propylene glycol monoisooctanoate, propylene glycol diisooctanoate, propylene glycol dicaprylate, etc. Examples of the ethylene glycol fatty acid esters include ethylene glycol monocaprylate, ethylene glycol dicaprylate, ethylene glycol monoisooctanoate, ethylene glycol diisooctanoate, etc. Examples of the glycerin fatty acid esters include glycerin monooleate, glycerin monostearate, glycerin monocaprylate, tetraglycerin monocaprylate, tetraglycerin hexacaprylate, etc. Examples of the polyoxyethylene fatty acid amides include polyoxyethylene stearic acid amide, coconut oil fatty acid diethanolamide, etc. Examples of the polyoxyethylene alkylamines include polyoxyethylene ethyleneoleylamine, etc.

In a preferred embodiment, the absorption-enhancing composition according to the present invention comprises, per 1 part by weight of a pantothenic acid derivative represented by the above general formula (I), from 1.4 to 2.9 parts by weight of triethyl citrate, from 6.8 to 14.1 parts by weight of polyoxyethylene-hardened castor oil serving as the nonionic surfactant, and from 4.4 to 9.2 parts by weight of propylene glycol monocaprylate.

The pantothenic acid derivatives represented by the above general formula (I) in the present invention are compounds disclosed in JP-A-3-218340 herein incorporated by reference.

The term "lower" as used in the definition of the pantothenic acid derivative of the general formula (I) means a linear or branched $C_{1-5}$ carbon chain. In the present invention, the pantothenic acid derivatives represented by the following general formula (II):

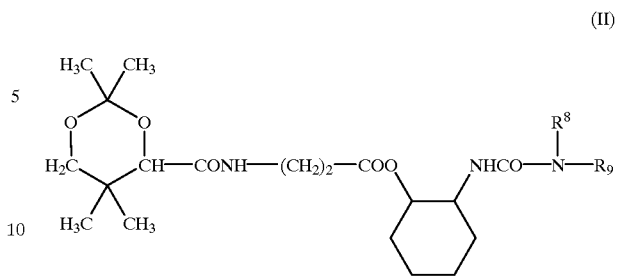

(II)

wherein $R^8$ represents a linear or branched $C_{3-10}$ hydrocarbon group and $R^9$ represents a linear or branched $C_{1-10}$ hydrocarbon group optionally substituted by phenyl group are preferable. Examples of the linear or branched $C_{1-10}$ hydrocarbon group include a linear and branched carbon chains such as methyl, ethyl, propyl, butyl, isopropyl, isobutyl, s-butyl, t-butyl, isopentyl, neopentyl (2,2-dimethylpropyl), pentyl, hexyl, heptyl, octyl, nonyl, decyl, etc. Examples of the linear or branched $C_{3-10}$ hydrocarbon group include a linear and branched carbon chains such as propyl, butyl, isopropyl, isobutyl, s-butyl, t-butyl, isopentyl, neopentyl (2,2-dimethylpropyl), pentyl, hexyl, heptyl, octyl, nonyl, decyl, etc. Examples of the $C_{1-10}$ hydrocarbon group substituted by phenyl group include a benzyl group, 2-pheylethyl group, 3-phenylpropyl group, etc. Examples of the pantothenic acid derivatives represented by the above general formula (I) include (1S,2S)-2-[3-(2,2-dimethylpropyl)-3-nonylureido]cyclohexan-1-yl 3-[(4R)-N-(2,2,5,5-tetramethyl-1,3-dioxane-4-carbonyl)amino] propionate, etc.

The absorption-enhancing compositions according to the present invention can be produced by a conventional methods employed in producing various preparations. For example, hard capsules can be prepared by adding a pantothenic acid derivative represented by the general formula (I) to a neutral or alcoholic ester and dissolving therein at room temperature, further adding a nonionic surfactant thereto, stirring the resulting mixture while heating it to 40 to 60° C. and then filling the resulting solution in hard capsules. Granules or tablets can be prepared by adsorbing the above-mentioned solution by a porous inorganic powder (for example, silicic anhydride) and then molding into granules or tablets.

Preferable examples of the dosage forms of the absorption-enhancing compositions for pantothenic acid derivatives according to the present invention include oral preparations such as soft capsules and hard capsules containing the compositions and granules and tablets wherein the compositions are solidified by adsorbing on porous powders, nasal drops, eye drops, lotions, injections, suppositories, etc.

The dose of the pantothenic acid derivative is generally from 1 to 1,000 mg/day in the case of oral administration, but the dose is not limited thereto.

To further illustrate the present invention in greater detail, and not by way of limitation, the following Examples, Referential Examples and Test Examples will be given.

Unless otherwise indicated, all parts, ratios, percentages, etc. in this specification are by weight.

Referential Example 1

To prepare a usual preparation for oral administration, (1S,2S)-2-[3-(2,2-dimethylpropyl)-3-nonylureido] cyclohexan-1-yl 3-[(4R)-N-(2,2,5,5-tetramethyl-1,3- dioxane-4-carbonyl)amino]propionate (hereinafter referred to as the "propionate compound") was processed into granules by the wet granulation method and then filled in hard capsules by using an encapsulation machine. Each capsule (No. 2) contained 375 mg of the granules.

Referential Example 2

Another absorption-enhancing composition preparation for the propionate compound was produced by the conventional method in the following manner. To 1 part of the propionate compound, 5 parts of oleic acid was added and dissolved at room temperature. Then, 5 parts of polyoxyethylene-hardened castor oil (Nikkol HCO60: manufactured by Nikko Chemicals, hereinafter referred to simply as HC) was added to the resulting solution and dissolved therein under heating to 40° C. The resulting solution was filled in hard capsules with the use of an encapsulation machine for oily/viscous materials. Each capsule (No. 4) contained 150 mg of the composition.

Referential Example 3

The capsules obtained in Referential Example 2 were coated with an enteric coating (methacrylate copolymer LD; manufactured by Rohm, hereinafter referred to as Eudragid) to give enteric capsules.

Test Example 1

The propionate compound preparations obtained in the above Referential Examples 1, 2 and 3 were orally administered in a dose of 90 mg/body to 3 rhesus monkeys having been fastened since the previous day. After the administration, the blood of each animal was collected with the passage of time and the concentration of the compound in the blood was measured by the following method. Table 1 shows the results.

(Measurement of Propionate Compound in Blood)

To 100 $\mu$L of the plasma were added 1 mL of a 30% aqueous solution of acetonitrile and 100 $\mu$L of the propionate compound-d6 (50 ng/mL) as an internal standard followed by stirring. Next, the resulting mixture was added to Bond Elut C18 which had been preliminarily equilibrated by passing about 2 mL portions of methanol, acetonitrile and purified water in this order. After washing with 2 mL of a 30% aqueous solution of acetonitrile and 2 mL of a 50% aqueous solution of acetonitrile, elution was performed with 1.8 mL of a 90% aqueous solution of acetonitrile. Then 30 $\mu$L of a 2.5% aqueous solution of ammonia was added thereto. After stirring, a 25 $\mu$L portion thereof was analyzed by high-performance liquid chromatography under the following conditions.

(Conditions for High-performance Liquid Chromatography)
Detector: Tandem type mass spectrometer.
Ionization method: Electrospray ion method.
Spray voltage: 4.5 KV.
Capillary temperature: 240° C.
Monitoring ion: Propionate compound and propionate compound-d6.
Column: CAPCELL PACK C18 UG-120 manufactured by Shiseido.
Column temperature: 40° C.
Mobile phase: Purified water (liquid A)/methanol (liquid B)=1/9. (The liquids A and B were mixed at a ratio of 1/9 and supplied.)

TABLE 1

Propionate compound absorption test
(Absorption at administration dose: 90 mg/body)

| Reference Example | Tmax (hr) | Cmax (ng/mL) | AUC (ng hr/mL) | Relative ratio of Cmax to Reference Example 1 |
|---|---|---|---|---|
| 1 | 11.0 | 6.0 | 63.0 | 1.0 |
| 2 | 1.0 | 34.0 | 111.0 | 5.7 |
| 3 | 7.0 | 34.0 | 243.0 | 5.7 |

As the data in Table 1 show, the conventional preparation obtained by filling wet-type granules into capsules showed Cmax of 6.0 ng/mL. This value was unsatisfactory as an oral preparation. Namely, it was judged that this preparation was hardly absorbable. In contrast, the gastric and enteric capsules produced as other conventional absorption-enhancing compositions each showed Cmax about 6 times higher than that of the product of Referential Example 1, as Table 1 shows. With respect to AUC, the enteric capsule showed an improved absorbability, i.e., about twice higher than that of the gastric capsule.

Test Example 2

The propionate compound preparations of Referential Examples 2 and 3 were each introduced into a glass bottle and stored in a sealed state at 60° C. for 1 week to thereby examine the properties and purity (yield of decomposition product, liquid chromatography). Table 2 shows the results.
(Determination of Decomposition Product)

0.075 g of the contents of each capsule was dissolved in 50 mL of the mobile phase to give a sample solution. 1 mL of this solution was precisely taken and the mobile phase was added thereto to give a total volume of 100 mL exactly, thus giving a standard solution. 20 $\mu$L portions of the sample solution and the standard solution were analyzed by high-performance liquid chromatography under the following conditions.

(Conditions for High-performance Liquid Chromatography)
Detector: UV absorption spectrometer.
Column: AM-312 manufactured by YMC.
Column temperature: 40° C.
Mobile phase: acetonitrile/water mixture (3:1).

TABLE 2

Stability test on propionate compound
(stored at 60° C., 1 week)

| Reference Example | Properties | | Purity test: Yield of analog/decomposition product (%) |
|---|---|---|---|
| | Appearance | Contents | |
| Reference Example 2 | no change | scarcely colored | 7.2 |
| Reference Example 3 | no change | scarcely colored | 7.2 |

As the results given in Table 2 show, the absorption-enhancing composition preparation of Referential Example 2 obtained by the conventional method was very unstable.

Referential Example 4

1 part of the propionate compound was added to 20 parts of propylene carbonate (manufactured by Showa Denko K.K.; hereinafter referred to simply as PC) and 20 parts of triethyl citrate (manufactured by Cultor Food Science; hereinafter referred to simply as TC) and dissolved therein at room temperature. The obtained solution was filled in hard capsules with the use of an encapsulation machine for oily/viscous materials. Each capsule (No. 2) contained 350 mg of the composition.

Referential Example 5

The procedure of Referential Example 4 was repeated but using 0.1 part of HC to give a propionate compound preparation composition.

EXAMPLE 1

To 1 part of the propionate compound was added 0.05 parts of PC. Further, 5 parts of HC was added thereto followed by dissolution with heating to 40° C. Next, the obtained solution was filled in hard capsules with the use of an encapsulation machine for oily/viscous materials. Each capsule (No. 2) contained 350 mg of the composition.

EXAMPLE 2

To 1 part of the propionate compound were added 1.6 parts of PC and 4.4 parts of propylene glycol monocaprylate (Sefsol; manufactured by Nikko Chemicals, hereinafter referred to simply as MG) followed by dissolution at room temperature. Next, 7.0 parts of HC was added to the obtained solution followed by dissolution with heating to 40° C. Then the resulting solution was filled in hard capsules with the use of an encapsulation machine for oily/viscous materials. Each capsule (No. 2) contained 350 mg of the composition.

EXAMPLE 3

The procedure of Example 2 was repeated but using 2.9 parts of PC, 14.1 parts of HC and 9.2 parts of MG to give a propionate compound preparation composition.

EXAMPLE 4

The procedure of Example 1 was repeated but using 8 parts of PC and 50.0 parts of HC to give a propionate compound preparation composition.

EXAMPLE 5

The procedure of Example 4 was repeated but using 3.0 parts of HC to give a propionate compound preparation composition.

EXAMPLE 6

The procedure of Example 5 was repeated but using 5.0 parts of HC to give a propionate compound preparation composition.

EXAMPLE 7

The procedure of Example 6 was repeated but using 40.0 parts of PC. The propionate compound preparation composition thus obtained was cooled to room temperature by allowing to stand and then filled in a vial to give a liquid preparation for internal use of the propionate compound.

EXAMPLE 8

The procedure of Example 1 was repeated but using TC as a substitute for the PC to give a propionate compound preparation composition.

EXAMPLE 9

The procedure of Example 8 was repeated but using 1.4 parts of TC, 6.8 parts of HC and 4.4 parts of MG to give a propionate compound preparation composition.

EXAMPLE 10

The procedure of Example 2 was repeated but using TC as a substitute for the PC to give a propionate compound preparation composition.

EXAMPLE 11

The procedure of Example 3 was repeated but using TC as a substitute for the PC to give a propionate compound preparation composition.

EXAMPLE 12

The procedure of Example 10 was repeated but using 6.8 parts of TC, 29.5 parts of HC and 19.3 parts of MG to give a propionate compound preparation composition.

EXAMPLE 13

The procedure of Example 6 was repeated but using TC as a substitute for the PC to give a propionate compound preparation composition.

EXAMPLE 14

The procedure of Example 2 was repeated but using polyoxyethylene sorbitan monooleate (Nikkol TO-10M; manufactured by Nikko Chemicals, hereinafter referred to simply as TW) as a substitute for the HC60. The resulting propionate compound preparation composition was molten at 32° C. and then filled in soft capsules with the use of a linear type device for automatically filling soft capsules. Each capsule (No. 5 of long) contained 350 mg of the composition.

The coating employed comprised 100 g of gelatin, 400 g of conc. glycerin, 30 g or ethylparaben and 10 g of propylparaben.

Test Example 3

As the result of evaluation of absorption-enhancing compositions prepared by the conventional method, it was confirmed that the absorbability in the digestive tracts could be improved by elevating the solubility. Thus, the compositions obtained in the above Examples 1 to 14 and Referential Examples 1 to 5 were examined in solubility. Table 3 summarizes the results.

TABLE 3

Solubility test on propionate compound

| Example or Reference Example | Solvent | | | Nonionic surfactant | | | | Solubility in water (μ/mL) | Relative ratio to Reference Example 1 |
|---|---|---|---|---|---|---|---|---|---|
| | PC | TC | total | HC | MG | TW | total | | |
| Example 1 | 0.05 | — | 0.05 | 5 | — | — | 5 | 4.3 | 86.0 |
| Example 2 | 1.6 | — | 1.6 | 7 | 4.4 | — | 11.4 | 27.6 | 552.0 |
| Example 3 | 2.9 | — | 2.9 | 14.1 | 9.2 | — | 23.3 | 23.9 | 478.0 |
| Example 4 | 8 | — | 8 | 50 | — | — | 50 | 25.9 | 518.0 |
| Example 5 | 8 | — | 8 | 3 | — | — | 3 | 4.9 | 98.0 |
| Example 6 | 8 | — | 8 | 5 | — | — | 5 | 8.2 | 164.0 |
| Example 7 | 40 | — | 40 | 5 | — | — | 5 | 6.3 | 126.0 |
| Example 8 | — | 0.05 | 0.05 | 5 | — | — | 5 | 4.0 | 80.0 |
| Example 9 | — | 1.4 | 1.4 | 6.8 | 4.4 | — | 11.2 | 26.3 | 526.0 |
| Example 10 | — | 1.6 | 1.6 | 7 | 4.4 | — | 11.4 | 28.0 | 560.0 |
| Example 11 | — | 2.9 | 2.9 | 14.1 | 9.2 | — | 23.3 | 24.8 | 496.0 |
| Example 12 | — | 6.8 | 6.8 | 29.5 | 19.3 | — | 48.8 | 27.1 | 542.0 |
| Example 13 | — | 8 | 8 | 5 | — | — | 5 | 6.1 | 122.0 |
| Example 14 | 1.6 | — | 1.6 | — | 4.4 | 7 | 11.4 | 16.0 | 320.0 |
| Reference Example 1 | granules | | — | — | — | — | — | 0.05 | 1.0 |
| Reference Example 2 | oleic acid | | — | 5 | — | — | 5 | 17.7 | 354.0 |
| Reference Example 3 | oleic acid/BC | | — | 5 | — | — | 5 | 17.7 | 354.0 |
| Reference Example 4 | 20 | 20 | 40 | — | — | — | — | 0.3 | 6.0 |
| Reference Example 5 | 20 | 20 | 40 | 0.1 | — | — | 0.1 | 0.6 | 12.0 |

Note:
The amounts of solvents and nonionic surfactants are expressed in parts by weight per 1 part by weight of the propionate compound.

The data given in Table 3 indicate that the solubility has been improved.

Test Example 4

The propionate compound preparation of Referential Example 1 and the enteric-coated ones of Examples 2 and 10 were orally administered in a dose of 75 mg/body to 3 rhesus monkeys having been fastened since the previous day. After the administration, the blood of each animal was collected with the passage of time and the concentration of the compound in the blood was measured by the same method as the one employed in Test Example 1. Table 4 shows the results.

TABLE 4

Propionate compound absorption test
(Absorption at administration dose: 75 mg/body)

| Example or Reference Example | Tmax (hr) | Cmax (ng/mL) | AUC (ng hr/mL) | Relative ratio of Cmax to Reference Example 1 |
|---|---|---|---|---|
| Reference Example 1 | 2.0 | 3.7 | 3.7 | 1.0 |
| Example 2 | 4.3 | 18.0 | 113.8 | 4.9 |
| Example 10 | 4.7 | 16.6 | 88.6 | 4.5 |

As the data in Table 4 show, the conventional preparation obtained by filling wet-type granules into capsules showed Cmax of 3.7 ng/mL, while the absorption-enhancing composition preparations with enteric coating showed each about 5 times higher Cmax than that of the product of Referential Example 1.

Test Example 5

The propionate compound preparations of Referential Example 2 and Examples 2 and 10 were each were each introduced into a glass bottle and stored in a sealed state at 60° C. for 1 week to thereby examine the properties and purity (yield of decomposition product, liquid chromatography) by the same methods as those employed in Test Example 2. Table 5 shows the results.

TABLE 5

Stability test on propionate compound
(stored at 40° C., 75% RH, 1 month)

| Example or Reference Example | Properties | | Purity test: Yield of analog/decomposition product (%) |
|---|---|---|---|
| | Appearance | Contents | |
| Example 2 | no change | no change | 0.6 |
| Example 10 | no change | no change | 0.5 |
| Reference Example 2 | no change | slightly colored | 8.1 |

As the results given in Table 5 show, the absorption-enhancing compositions according to the present invention were stable.

It has been confirmed that the compositions according to the present invention, which are prepared by dissolving the pantothenic acid derivative represented by the above general formula (I) in a neutral or alcoholic ester and adding a nonionic surfactant or a mixture thereof, have an enhanced solubility in water and exhibit an absorption-enhancing effect. Moreover, these compositions are stable and show an elevated bioavailability rate of the pantothenic acid derivative represented by the general formula (I), which enlarges the application range thereof as drugs.

While the invention has been described in detail and with reference to specific embodiments thereof, it will be apparent to one skilled in the art that various changes and modifications can be made therein without departing from the spirit and scope thereof.

This application is based on Japanese patent application No. Hei. 10-309639 filed on Oct. 30, 1998, incorporated herein by reference.

What is claimed is:

1. An absorption-enhancing composition for a pantothenic acid derivative, which comprises a pantothenic acid derivative represented by the following general formula (I), a neutral or alcoholic ester, and a nonionic surfactant:

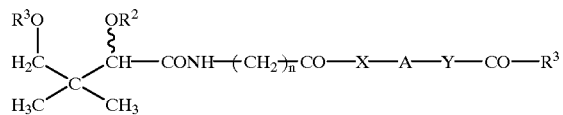

(I)

wherein
  $R^1$ and $R^2$ are the same or different and each independently represents a hydrogen atom or a hydroxyl-protective group or $R^1$ and $R^2$ together represent a hydroxyl-protective group;
  $R^3$ represents a saturated or unsaturated, linear, branched or cyclic $C_{5-25}$ monovalent aliphatic hydrocarbon group optionally substituted by an aromatic group, or an amino group represented by the formula $-N(R^4)R^5$ (wherein $R^4$ represents a saturated or unsaturated, linear, branched or cyclic $C_{3-25}$ monovalent aliphatic hydrocarbon group; and $R^5$ represents a hydrogen atom or a saturated or unsaturated, linear, branched or cyclic monovalent aliphatic hydrocarbon group optionally substituted by an aromatic group);
  A represents a saturated or unsaturated, linear, branched or cyclic $C_{2-16}$ divalent aliphatic hydrocarbon group, divalent aromatic hydrocarbon group or divalent heteroaryl group optionally substituted by an aromatic group;
  one of X and Y represents an amino group represented by the formula $-N(R^6)-$ while the other represents $-O-$, $-S-$ or an amino group represented by the formula $-N(R^7)-$ (wherein $R^6$ and $R^7$ represent each a hydrogen atom or a lower alkyl group); and
  n is an integer of from 1 to 4.

2. The composition as claimed in claim 1, wherein the pantothenic acid derivative is represented by the following general formula (II):

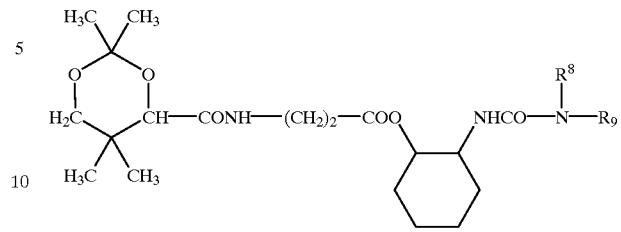

(II)

wherein wherein $R^8$ represents a linear or branched $C_{3-10}$ hydrocarbon group and $R^9$ represents a linear or branched $C_{1-10}$ hydrocarbon group optionally substituted by phenyl group.

3. The composition as claimed in claim 1, wherein the pantothenic acid derivative is (1S,2S)-2-[3-(2,2-dimethylpropyl)-3-nonylureido]cyclohexan-1-yl 3-[(4R)-N-(2,2,5,5-tetramethyl-1,3-dioxane-4-carbonyl)amino]propionate.

4. The composition as claimed in claim 1, wherein said neutral or alcoholic ester is a carbonic acid diester or an oxy-acid ester.

5. The composition as claimed in claim 1, wherein said nonionic surfactant is a nonionic surfactant of the ether type, the ether ester type, the ester type or the nitrogen-containing type.

6. The composition as claimed in claim 4 or 5, which contains from 0.5 to 10 parts by weight of said neutral or alcoholic ester and from 1 to 25 parts by weight of said nonionic surfactant per 1 part by weight of said pantothenic acid derivative.

7. The composition as claimed in claim 6, wherein said neutral or alcoholic ester is triethyl citrate and said nonionic surfactant is polyoxyethylene-hardened castor oil and/or propylene glycol monocaprylate.

8. The composition as claimed in claim 7, which contains from 1.4 to 2.9 parts by weight of triethyl citrate, from 6.8 to 14.1 parts by weight of polyoxyethylene-hardened castor oil and from 4.4 to 9.2 parts by weight of propylene glycol monocaprylate per 1 part by weight of said pantothenic acid derivative.

* * * * *